(12) United States Patent
Shen et al.

(10) Patent No.: US 12,194,192 B2
(45) Date of Patent: Jan. 14, 2025

(54) TISSUE SCAFFOLD FOR USE IN TENDON AND/OR LIGAMENT

(71) Applicant: INDUSTRIAL TECHNOLOGY RESEARCH INSTITUTE, Hsinchu (TW)

(72) Inventors: Hsin-Hsin Shen, Hsinchu (TW); Pei-I Tsai, Hsinchu (TW); Chih-Chieh Huang, Hsinchu (TW); Chien-Cheng Tai, Hsinchu (TW); Yi-Hung Wen, Hsinchu (TW); Jeng-Liang Kuo, Hsinchu (TW); Chun-Hsien Ma, Hsinchu (TW); Lih-Tao Hsu, Hsinchu (TW); Shin-I Huang, Hsinchu (TW); Kuo-Yi Yang, Hsinchu (TW); Tsung-Hsien Wu, Hsinchu (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 862 days.

(21) Appl. No.: 17/136,077

(22) Filed: Dec. 29, 2020

(65) Prior Publication Data

US 2022/0202990 A1 Jun. 30, 2022

(51) Int. Cl.
*A61L 27/24* (2006.01)
*A61F 2/08* (2006.01)
(Continued)

(52) U.S. Cl.
CPC ............... *A61L 27/24* (2013.01); *A61F 2/08* (2013.01); *A61F 2/0811* (2013.01); *A61L 27/10* (2013.01);
(Continued)

(58) Field of Classification Search
CPC .......... A61L 27/24; A61L 27/10; A61L 27/26; A61L 2002/30009; A61F 2/08; A61F 2/0811; C08L 75/04
See application file for complete search history.

(56) References Cited

U.S. PATENT DOCUMENTS

| 5,004,474 A * | 4/1991 | Fronk .................... A61F 2/08 623/13.14 |
| 6,599,319 B2 | 7/2003 | Knudsen et al. |

(Continued)

FOREIGN PATENT DOCUMENTS

| CN | 102908210 | 6/2015 |
| CN | 107510520 | 12/2017 |

(Continued)

OTHER PUBLICATIONS

Extended European Search Report for European Patent Application No. 21193592.9 dated Feb. 17, 2022.
(Continued)

*Primary Examiner* — Jerrah Edwards
*Assistant Examiner* — Aren Patel
(74) *Attorney, Agent, or Firm* — Amin, Turocy & Watson, LLP

(57) ABSTRACT

A tissue scaffold for use in a tendon and/or ligament is provided, which includes a weave formed by interlacing warp yarns and weft yarns, wherein the warp yarns include a plurality of fibers with an alternative shaped cross section structure, and the weave includes: a main body area with a bioactive component formed on the fiber surface, and a fixed area comprises the weft yarn having a bioceramic material. The tissue scaffold prepared in the present disclosure has the characteristics of stimulating the growth of tissues and inducing tissue repair, effectively improving the ability of
(Continued)

tissue regeneration and bone healing, and is beneficial to the reconstruction of the tendon and/or ligament.

9 Claims, 14 Drawing Sheets

(51) Int. Cl.
  *A61L 27/10* (2006.01)
  *A61L 27/26* (2006.01)
  *A61F 2/30* (2006.01)
  *C08L 75/04* (2006.01)

(52) U.S. Cl.
  CPC ..... *A61L 27/26* (2013.01); *A61F 2002/30009* (2013.01); *C08L 75/04* (2013.01)

(56) References Cited

U.S. PATENT DOCUMENTS

| | | | |
|---|---|---|---|
| 7,494,506 | B2 | 2/2009 | Brulez et al. |
| 7,700,147 | B2 | 4/2010 | Brulez et al. |
| 10,201,635 | B2 * | 2/2019 | Reves ................ A61K 38/1875 |
| 2006/0280775 | A1 * | 12/2006 | Ashammakhi .......... A61L 27/58 |
| | | | 623/1.11 |
| 2010/0158976 | A1 * | 6/2010 | O'Brien ................ A61K 47/02 |
| | | | 514/21.5 |
| 2016/0228608 | A1 * | 8/2016 | Hakimi ................. A61L 27/18 |
| 2017/0172736 | A1 * | 6/2017 | Chadha ................. D03D 27/02 |
| 2018/0028317 | A1 * | 2/2018 | Schlachter ............ A61F 2/2846 |
| 2019/0269822 | A1 * | 9/2019 | Williams ................ C08L 65/00 |
| 2019/0350690 | A1 * | 11/2019 | Koob .................... A61L 31/044 |
| 2021/0008246 | A1 * | 1/2021 | Ameer .................. B33Y 10/00 |

FOREIGN PATENT DOCUMENTS

| | | |
|---|---|---|
| CN | 110680558 | 1/2020 |
| CN | 111345920 | 6/2020 |
| CN | 111359012 | 7/2020 |
| CN | 111450316 | 7/2020 |
| CN | 111544654 | 8/2020 |
| CN | 112030556 | 12/2020 |
| JP | 2005-124959 | 5/2005 |
| JP | 2010-115412 | 5/2010 |
| TW | 201726997 | 8/2017 |
| TW | I692559 | 5/2020 |

OTHER PUBLICATIONS

Wang, et al. "Biological and Biomechanical Evaluation of Autologous Tendon Combined with Ligament Advanced Reinforcement System Artificial Ligament in a Rabbit Model of Anterior Cruciate Ligament Reconstruction", Orthopaedic Surgery; Jan. 14, 2018; 144-151.
Saleem, et al. "Silk fibroin/ hydroxyapatite scaffold: a highly compatible material for bone regeneration", Science and Technology of Advanced Materials; Mar. 25, 2020; 242-266.
Zhang, et al. "Local delivery of controlled-release simvastatin to improve the biocompatibility of polyethylene terephthalate artificial ligaments for reconstruction of the anterior cruciate ligament", International Journal of Nanomedicine; Jan. 27, 2016; 465-478.
Li, et al. "Remnant Repair-enhanced Polyethylene Terepthalate Artificial Ligament Graft Ligamentization", Orthopedics and Biomechanics; Apr. 13, 2015; 1015-1020.
Jiang, et al. "Enhancement of osseointegration of polyethylene terephthalate artificial ligament by coating of silk fibroin and depositing of hydroxyapatite", International Journal of Nanomedicine Dovepress; Sep. 29, 2014; 4569-4580.
Nishimoto, et al. "Ligament regeneration using an absorbable stent-shaped poly-L-lactic acid scaffold in a rabbit model", International Orthopaedics; Aug. 29, 2012; 2379-2386.
Cai, et al. "Silk fibroin and hydroxyapatite segmented coating enhances graft ligamentization and osseointegration processes of the polyethyleneterephthalate artificial ligament in vitro and in vivo", Journal of Materials Chemistry B; Aug. 14, 2018; 5738-5749.
Wang, et al. "Enhance the biocompatibility and osseointegration of polyethylene terephthalate ligament by plasma spraying with hydroxyapatite in vitro and in vivo", International Journal of Nanomedicine; Jun. 25, 2018; 3609-3623.
Al, et al. "Effect of PET graft coated with silk fibroin via EDC/NHS crosslink on graft-bone healing in ACL reconstruction", RSC Advances; Nov. 3, 2017; 51303-51312.
Zhi, et al. "Silk Enhances Ligamentization of Polyethylene Terephthalate Artificial Ligament in a Canine Anterior Cruciate Ligament Reconstruction Model", Artif Organs; Dec. 13, 2018; E94-E108.
Chinese Office Action for Chinese Patent Application No. 202011592525.0 dated May 20, 2024.

* cited by examiner

TISSUE SCAFFOLD FOR USE IN TENDON AND/OR LIGAMENT

BACKGROUND

Technical Field

This disclosure relates to scaffolds for use in tissue engineering, in particular to a tissue scaffold for use in a tendon and/or ligament injury.

Description of Related Art

Tear or rupture of a tendon or ligament is a common clinical sports injury, especially when the injury occurs on the cruciate ligament in the knee joint. Due to biological environment and limited blood supply of the ligament tissue, it does not have the ability to heal naturally after it is ruptured, and needs to be reconstructed through surgery.

Regarding the reconstruction of tendons or ligaments, it can be divided into autograft, allograft and artificial graft according to the type of repair material. Although autografts have good reconstruction effects and no immune rejections, there are problems such as complications at donor site. Allografts are not only costly, but also have the risk of immune rejection and disease transmission. By contrast, because of its convenient materials, no risk of disease transmission, and high mechanical strength, artificial grafts have gradually attracted the attention of the medical community recently. However, artificial grafts only have mechanical load-bearing effects, and do not have biological activities and tissue inductions, which are not good for the healing of tendons/ligaments and bone interface. Further, the cells and tissues on the surface of the artificial ligament are difficult to grow to form a normal tendon or ligament tissue. After a long-term use, the artificial graft is prone to fatigue, abrasion, and fracture, which can lead to instability of the knee joint, and the wear fragments can easily cause iatrogenic injury such as water accumulation in the joint cavity.

Accordingly, it is necessary to propose a tissue scaffold with a biological activity and tissue induction to improve fatigue, abrasion, fracture and poor stability of existing artificial grafts after long-term use.

SUMMARY

The disclosure provides a tissue scaffold for use in a tendon and/or ligament, which comprises a weave formed by interlacing warp yarns and weft yarns, wherein the warp yarns include a plurality of fibers with an alternative shaped cross section structure. The weave comprises a main body area, wherein a bioactive component is on the fiber surface of the main body area, and the bioactive component can be further impregnated into the pores of the main body area; and a fixed area, wherein the fixed area is formed on the two sides of the main body area, and the weft yarns comprises a bioceramic material.

According to the present disclosure, through the design of a unique weave structure, and the corresponding bioactive materials are respectively combined according to the tissue scaffold sections, to provide more cell attachment area and a good proliferation environment, effectively enhancing the activity and proliferation capacity of soft and bone tissues. It can be provided for the reconstruction of tendon and/or ligament tissue, and it has application prospects.

BRIEF DESCRIPTION OF DRAWINGS

The embodiments of the present disclosure are explained by referring to the drawings as examples.

DETAILED DESCRIPTION

The following is a description of the implementation of the present disclosure through specific embodiments. A person having ordinary skill in the art can easily understand the advantages and effects of the present disclosure from the content disclosed in this specification. The present disclosure can also be implemented or applied by other different implementations, and various details in this specification can also be based on different viewpoints and applications, without departing from the spirit disclosed in the present disclosure, with different modifications and changes. In addition, all ranges and values herein are inclusive and combinable. Any value or point falling within the range described herein, for example, any integer can be used as the minimum or maximum value to derive the lower range, etc.

Figure 1:
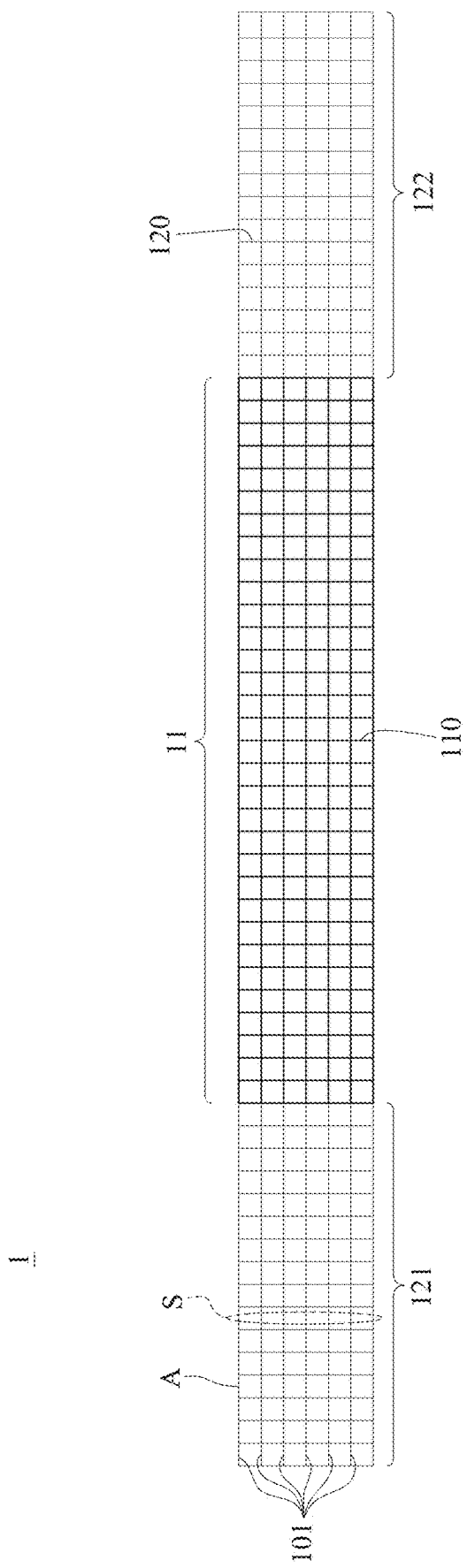
FIG. 1 is a schematic diagram of a tissue scaffold according to an exemplary embodiment.

According to the present disclosure, a tissue scaffold for use in a tendon and/or ligament is provided. As shown in FIG. 1, a tissue scaffold 1 is constituted by a weave formed by interlacing warp yarns 101 and weft yarns 110 and 120. The warp yarn 101 comprises a plurality of fibers with an alternative shaped cross section structure, and the plurality of fibers constitute the warp yarn. The weave comprises a main body area 11 containing a bioactive component on a surface thereof, and the bioactive component may be further impregnated into the pores of the main body area 11; and fixed areas 121 and 122 containing the bioceramic material weft yarn 120 being formed on two sides of the main body area.

The term "warp yarn" used herein refers to the yarn that extends along the length of a loom during weaving and is used as the main support structure in the weave, and the direction is the same as that of tension when performing the stretching action of tendons and/or ligaments. Further, as shown in FIG. 1, the warp yarn 101 comprises a plurality of fibers having a long axis A along the length of the tissue scaffold 1, and the warp yarn 101 of the main body area 11 and the fixed area 121 and 122 of the tissue scaffold of the present disclosure are integrally formed. On the other hand, the term "weft yarn" refers to yarns interlaced or perpendicular with the warps.

The above-mentioned warp yarns and the weft yarns are formed by twisting and drawing multiple fibers. In a specific embodiment, the warp yarns in the tissue scaffold of the present disclosure are twisted into 200 to 800 denier, the weft yarns are twisted into 50 to 100 denier.

The term "weave" used herein is woven by warp yarns and weft yarns in an interlaced and or mutually perpendicular manner, and the interweaving points formed thereby may be arranged continuously or discontinuously, and the positions of the interweaving points may be selected periodically or irregularly.

In one embodiment, the pore size of the weave of the tissue scaffold of the present disclosure is 0.1 to 1 mm, and the pore of the weave provides sufficient growth space for cells and provides the transportation space for gas exchange, nutrient and metabolism required during cells growth.

On the other hand, the weave of the disclosure is not limited to a single-layer weaving structure, but also includes a multi-layer upper and lower weaving structure. In another embodiment, the thickness or diameter of the weave is 1.0 to 10 mm.

In the tissue scaffold of the present disclosure, the material of the weave can be a polymer material or a polymer composite material, wherein the polymer composite material comprises other fillers, such as carbon fiber, in addition to the polymer material. The polymer material is selected in consideration of the mechanical properties, stability, abrasion resistance and biocompatibility thereof, but is not limited thereto.

In an exemplary embodiment, the polymer material may be one of polyethylene terephthalate, polyethylene, polytetrafluoroethylene, polyurethane, polycaprolactone, polylactic acid, polyglycolic acid, polyether ether ketone, polyether ketone ketone, or a mixture or copolymer thereof, wherein polyethylene may include ultra-high molecular weight polyethylene.

In another specific embodiment, the material of the above-mentioned weave is polyethylene terephthalate.

Figure 8A:
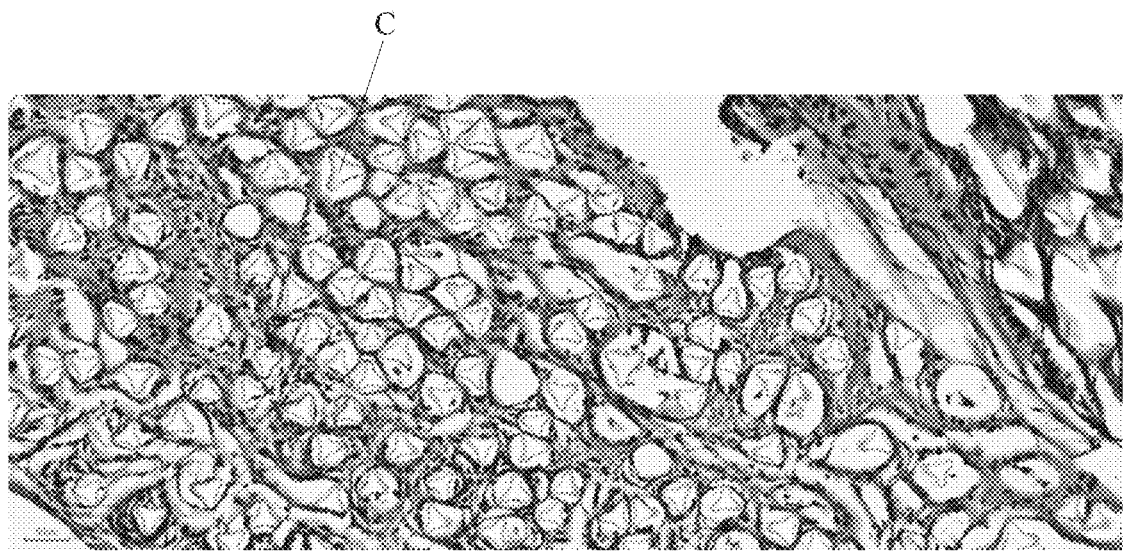
FIG. 8A to 8B are the tissue sections stained with hematoxylin-eosin and Masson's trichrome of the tissue scaffold, respectively, of the embodiments according to the present disclosure.

The term "alternative shaped cross section structure" used herein refers to a fiber structure with a non-circular cross-section, which has a relatively high fiber surface area and brings the effect of enhancing the adhesion of cells. In one embodiment, the alternative shaped cross section structure of the warp yarn fiber of the present disclosure may comprise a H-shaped cross-section, a S-shaped cross-section, a W-shaped cross-section, a Y-shaped cross-section, or a cross-shaped cross-section. For example, the alternative shaped cross section structure C is Y-shaped cross-section in FIGS. 8A and 8B.

Figure 2:
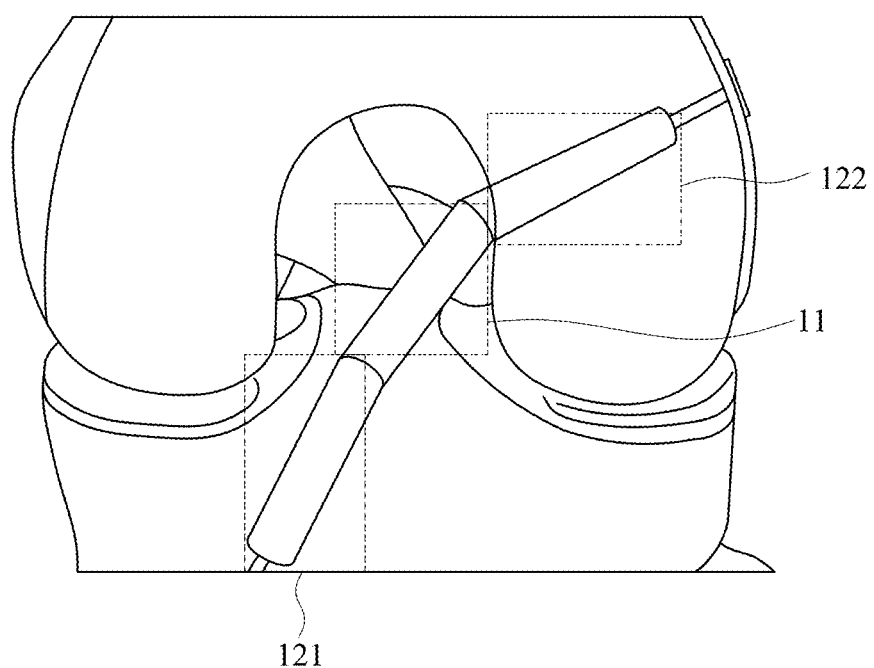
FIG. 2 is a schematic diagram of an actual use state of the tissue scaffold according to an exemplary embodiment.

In the tissue scaffold of the present disclosure, the fiber's thickness of the weave corresponds to the overall surface area, which affects the surface properties and mechanical properties of the weave. In another embodiment, the diameter of the long axis of the fibers with the alternative shaped cross section structure comprised in the warp yarn is 15 to 50 micrometers, and the fibers' diameter of the weft yarn constituting the weave is 20 to 50 micrometers. In another embodiment, the fineness of the fibers with the alternative shaped cross section structure comprised in the warp yarn is 1.5 to 50 denier, and the fineness of the fibers of the weft yarn constituting the weave is 40 to 100 denier. As shown in FIG. 2, FIG. 2 illustrates the actual implementation of the tissue scaffold of the present disclosure. The "main body area" 11 refers to the part of the weave exposed outside the bone, and the "fixed area" 121 and 122 refers to the part of the weave implanted in bone, for example, used to the bone connected with the original tendon and/or ligament tissue.

In order to further induce tendon and/or ligament tissue repair, there is a bioactive component on the fiber surface of the main body area, and the bioactive component can be further impregnated into the pores of the main body area to increase cell proliferation ability, wherein the bioactive component is collagen.

In one embodiment, the modification of tissue scaffold comprising the bioactive component of the present disclosure is prepared by the following steps of:

providing a reaction solution comprising a bioactive component; and bringing the main body area into contact with the reaction solution.

The term "reaction solution" includes a solvent and a pH adjusting agent in addition to a bioactive component.

The above bioactive component includes collagen, gelatin, silk protein, and the like.

In another embodiment, the bioactive component comprises collagen, and the collagen accounts for 0.5 to 5% by weight of the total weight of the main body area.

In embodiments, the weight ratio of the collagen to the total weight of the main body area may be about 0.6, 0.7, 0.8, 0.9, 1.0, 1.5, 2.0, 2.5, 3.0, 3.5, 4.0 or 4.5% by weight, and but it is also not limited thereto.

In exemplary embodiment, in the mentioned above reaction solution, the bioactive component is collagen. The solvent is an aqueous acetic acid solution with pH≤3.0. The pH adjusting agent is phosphate buffered saline and sodium hydroxide. The specific preparation method comprises: dissolving 0.1 g of the collagen powder in a 60 ml of an aqueous acetic acid solution, adding 1 g of the main body area of the weave, then adding 40 ml of phosphate buffered saline and adjust the pH to 7.5 with sodium hydroxide. So that the collagen is formed on the fiber surface of the main body area.

In another embodiment, the solid content of the collagen dissolved in the acetic acid is 0.01 to 0.1% by weight, and the reaction temperature of the main body area and the reaction solution is 20 to 40° C., and the reaction time is 24 to 48 hours.

In addition, the main body area of the present disclosure can be modified to comprise other cell proliferation stimulating components, such as gelatin, silk protein, keratin, and the like.

Regarding the mentioned above weft yarn of the fixed area, in order to effectively enhance the healing ability of the bone interface, a bioceramic material is added into it. In one embodiment, the bioceramic material is, for example, calcium phosphate, calcium sulfate, bioglass or a combination of the foregoing. In one embodiment, the calcium phosphate may be hydroxyapatite or tricalcium phosphate.

In another embodiment, the bioceramic material is hydroxyapatite, and an average particle size thereof is about 10 to 200 nanometers.

In one embodiment, the bioceramic material is present in the weft yarn of the fixed area, and the bioceramic material accounts for 1 to 4% by weight of the total weight of the weft yarn of the fixed area. In another embodiment, the bioceramic material accounts for more than 1% to 4% by weight of the total weight of the weft yarn in the fixed area. When the weight ratio of bioceramic materials is too low, the bone growth cannot be enhanced. If the weight ratio of the bioceramic material is too high, it is easy to break when spinning the fiber.

In other embodiments, the weight ratio of the bioceramic material to the total weight of the weft yarns of the fixed area may be about 1.5, 2.0, 2.5, 3.0, or 3.5% by weight, and is not limited thereto.

On the other hand, the weft yarns comprising the bioceramic material and the weft yarns free of bioceramic material may be selected in the fixed area of the present disclosure, or the bioceramic material may be included in each weft yarn. In exemplary embodiment, the ratio of weft yarns comprising the bioceramic material to the weft yarns free of bioceramic material is about 1:9 to 10:0. In another embodiment, the weft yarns comprising the bioceramic material can be used alone in the fixed area of the present disclosure.

For the weft fiber comprising the bioceramic material in the fixed area of the tissue scaffold of the present disclosure, it is prepared by the following steps of:
providing a masterbatch mixed with bioceramic materials; and
spinning with the masterbatch.

In a specific embodiment, the masterbatch comprises the above weave material and bioceramic material, and the content of the bioceramic material accounts for 1 to 4% by weight of the masterbatch.

In addition to the above weave material and bioceramic material, the masterbatch system also comprises a dispersant. The dispersant may be a polyester polymer material, and the content of the dispersant accounts for 0.1 to 2% by weight of the masterbatch.

In one embodiment, the specific preparation method of the masterbatch comprises the steps of: subjecting the polyethylene terephthalate, hydroxyapatite and polyester dispersant to mixing and granulation to form the masterbatch.

The disclosure will be further described in detail below through specific embodiments, but the scope of the disclosure is not limited by the description of the embodiments.

Example 1: Preparation of a Tissue Scaffold

Preparation of a warp yarn: polyethylene terephthalate was subjected to hot melt spinning to obtain a semi-stretched yarn through a modified cross-section spinning nozzle at a temperature of 270° C. or higher, and then stretched at a temperature of 100 to 200° C. to obtain a fully stretched yarn.

Preparation of a weft yarn: the preparation method of the weft yarn was the same as the above preparation method of the warp yarn, except that the modified cross-section spinning nozzle was adjusted to a circular spinning nozzle.

When preparing the weft yarns comprising bioceramics, bioceramics-incorporated masterbatch was used, wherein the method for preparing bioceramics-incorporated masterbatch was prepared by the following steps of: mixing polyethylene terephthalate, hydroxyapatite with an average particle size of 60 nm, and polyester dispersan, and granulating the mixture to form a masterbatch with 2% by weight of the bioceramic material.

Preparation of the weave: according to the main body area and fixed area of the weave shown in FIG. 1, the warp yarns and the weft yarns were selected for interlaced weaving, and the main body area was brought into contact with the reaction solution comprising the bioactive components.

Regarding the above reaction solution, collagen was taken as the bioactive component. In addition to the bioactive component, the reaction solution also included a solvent and pH adjusting agents, wherein the solvent was an aqueous acetic acid solution with pH≤3.0, and the pH adjusting agents were phosphate buffered saline and sodium hydroxide. The specific modification method thereof includes the following steps for preparation: dissolving 0.1 g of the collagen powder in a 60 ml of an aqueous acetic acid solution, adding 1 g of the main body area of the weave, then adding 40 ml of phosphate buffered saline and adjust the pH to 7.5 with sodium hydroxide, and after 48 hours of reaction at a reaction temperature of 20 to 40° C., forming collagen on the fiber surface of the main body area.

Figure 3:
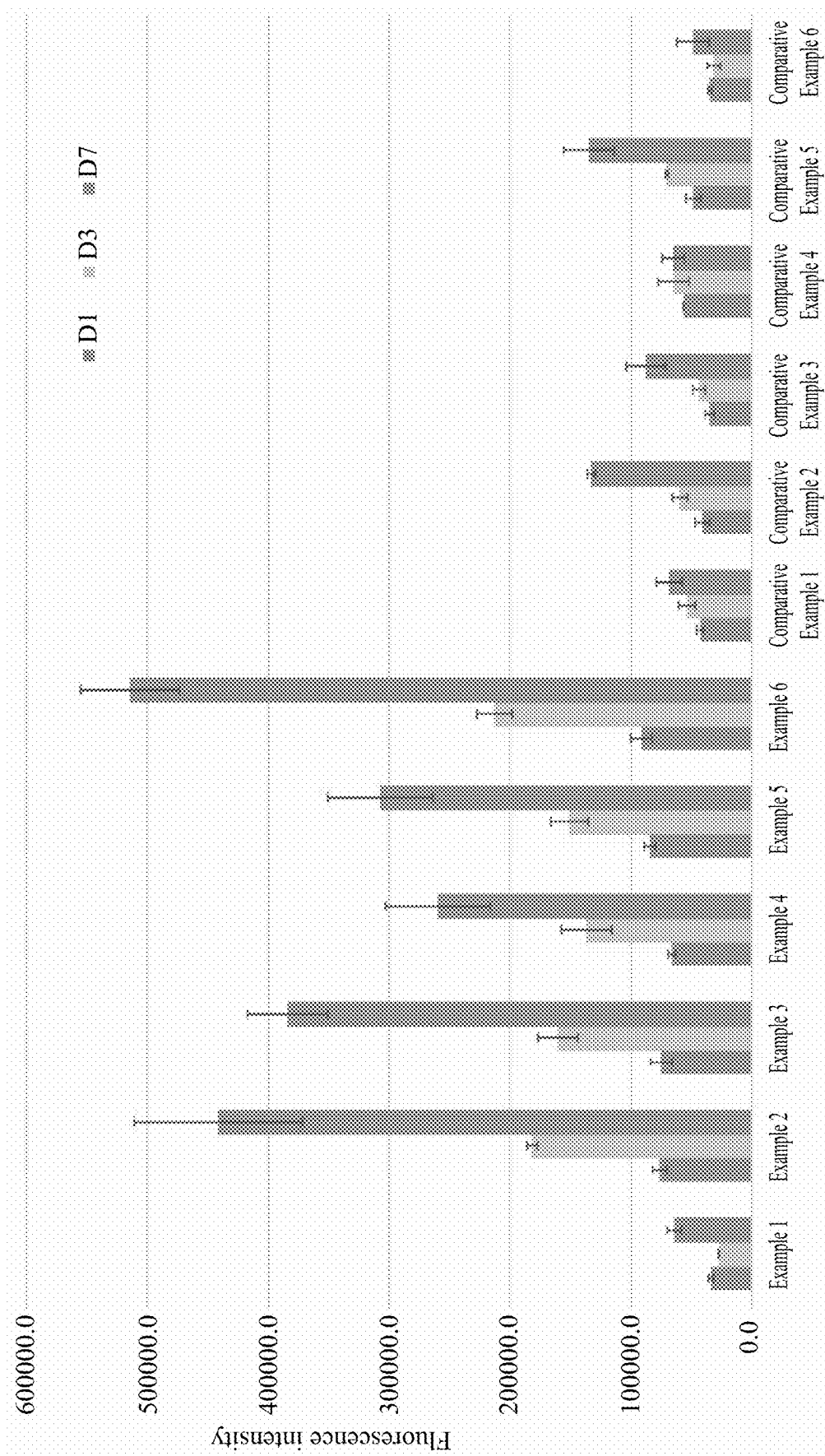
FIG. 3 is a comparison diagram of the number of proliferated cells of the tissue scaffolds between the embodiments and comparative examples, wherein each group of the embodiments and comparative examples are D1, D3, and D7 from left to right respectively, and D1, D3, and D7 show the number of cells cultured on the fiber surface of the weaves for 1, 3 and 7 days, respectively.
Figure 4:
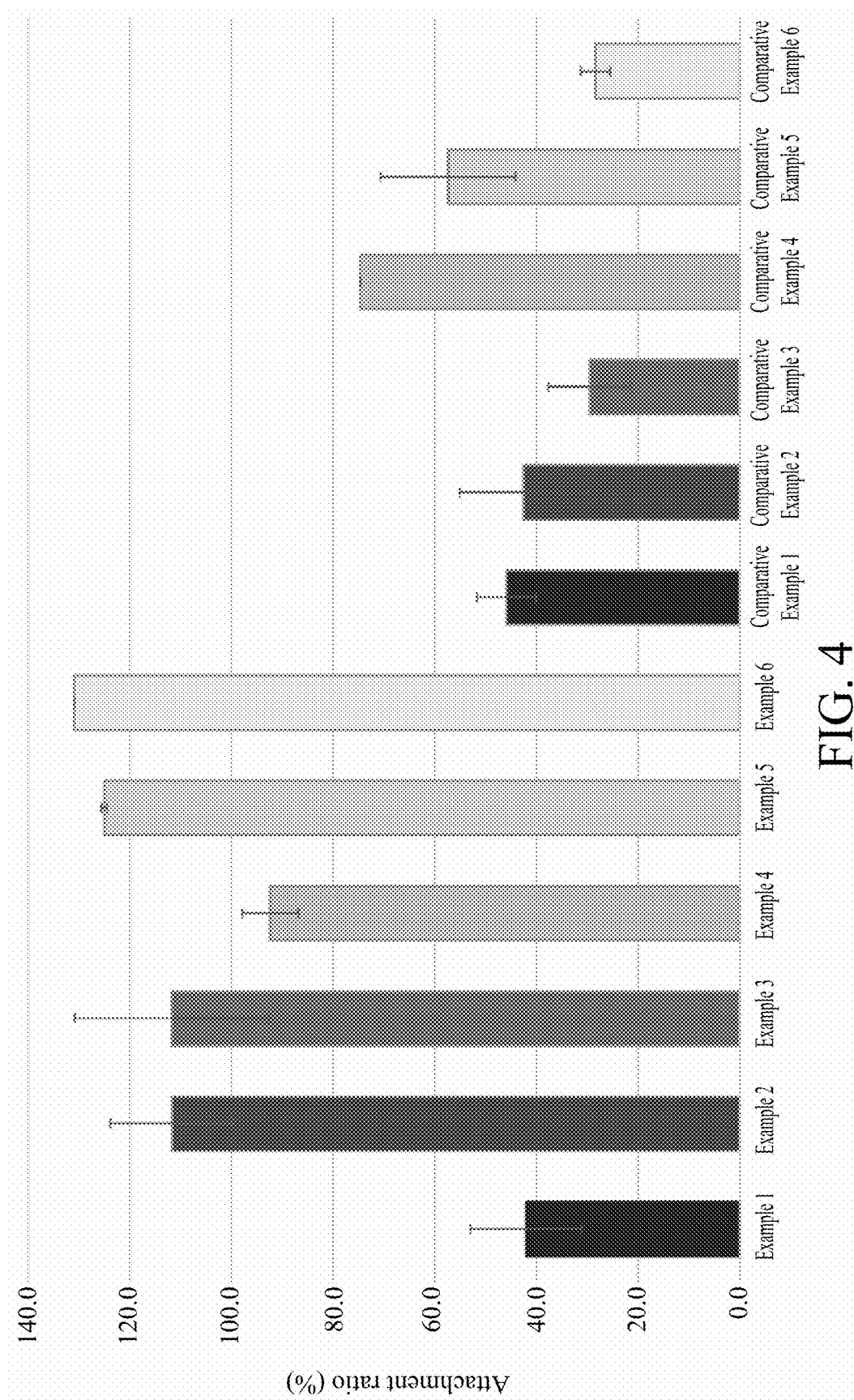
FIG. 4 is a comparison diagram of the cell attachment ratios of tissue scaffolds of the embodiments and comparative examples according to the present disclosure.

Finally, the weave of the tissue scaffold prepared above was cut into an appropriate size, and the following cell tests and analysis were performed:

(1) Determination of the number of cell proliferation and cell attachment ratio: A weave (1 cm$^2$) of the main body area of the present embodiment was taken and placed in a 48-well plate, a small amount of cell suspension (20 µl) was dropped on the surface, and placed in an incubator at 37° C. for 2 hours. 0.8 ml of bone marrow mesenchymal stem cell culture medium was added, and the unattached cells was taken away from the fiber surface of the weave by the culture medium. After overnight incubation, the weave attached with cells was transferred to a new 48-well plate, 0.3 ml of PrestoBlue was and performed in an incubator at 37° C. PrestoBlue was reduced to pink by nicotine adenine dinucleotide (NADH) dehydrogenase in mitochondria, the number of reacted cells could be detected by fluorescence (Ex/Em: 560 nm/590 nm). After 1 hour of reaction, 100 ul of the reactant was removed and transferred to a 96-well plate for analysis to detect a fluorescence read (Ex/Em: 560 nm/590 nm) thereof. The number of cells attached to the fiber surface was quantified by interpolation according to the standard curve, and the results of the number of cell proliferation and the cell attachment ratio are recorded in FIG. 3 and FIG. 4 respectively. From the results in FIGS. 3 and 4, it is known that the tissue scaffold of the present embodiment brings the effect of significantly improving cell proliferation and cell adhesion due to the surface modification of the warp yarn fiber with an alternative shaped cross section structure and the main body area of the weave.

Figure 5:
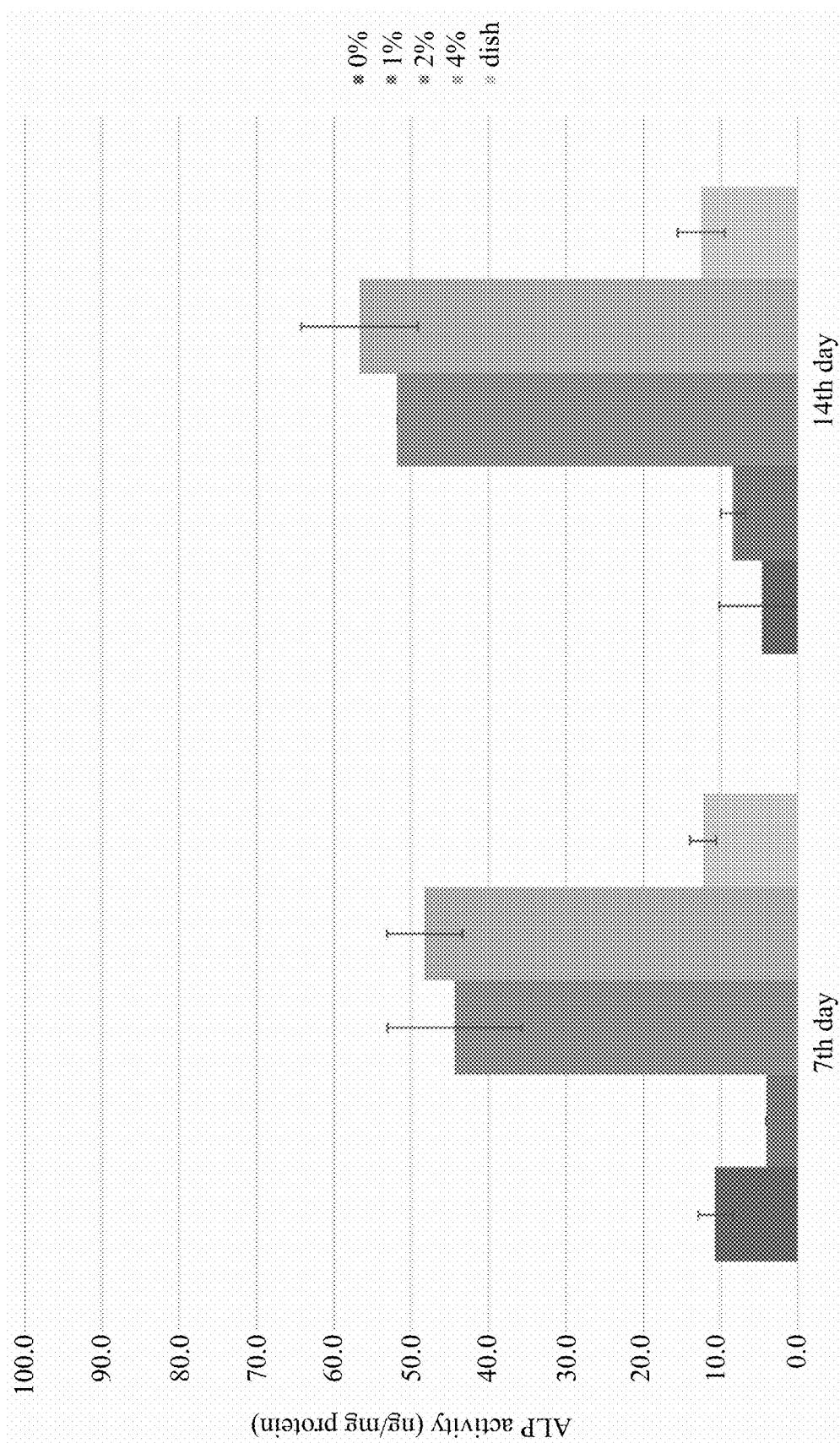
FIG. 5 is a comparison diagram of the osteogenic enzyme ALP activity on the 7th and 14th days of cell culture of the tissue scaffolds of the embodiments and comparative examples, wherein each group on the 7th and 14th days are 0%, 1%, 2%, 4% and dish from left to right, 0% indicates the surface culture of the woven fiber without adding the bioceramic material in comparative example 8; 1% indicates the surface culture of the woven fiber containing the bioceramic material of 1% by weight in comparative example 9; 2% indicates the surface culture of the woven fiber containing the bioceramic material of 2% by weight in embodiment 1; 4% indicates the surface culture of the woven fiber containing the bioceramic material of 4% by weight in embodiment 6; dish means the osteogenic enzyme ALP activity results which are only cultured on the cell culture plate but not on the surface of the woven fiber as a control.

(2) Determination of ALP activity of osteogenic enzyme: mesenchymal stem cells (MSC) were used to determine the activity of osteogenic enzyme ALP. The cell seeding density was $5 \times 10^4/cm^2$, the bone differentiation medium contained α-MEM containing 10% fetal bovine serum (FBS), ascorbic acid (50 µg/ml), dexamethasone (0.1 µM), and β-sugar phosphate (10 mM), and the control medium contained α-MEM containing 10% FBS. Samples were collected on the 7th and 14th days for analysis. A pNPP alkaline phosphatase detection kit (SensoLyte®) and a Microplate reader (Biotek, Synergy™ H1) were used to measure the activity of osteogenic enzyme ALP, and the results are recorded in FIG. 5. The results of the ALP activity of the cell culture plate (dish) were used as a control. It is obvious that the tissue scaffold of the present embodiment enhancing the effect of the activity of the osteogenic enzyme ALP due to comprising the bioceramic materials, and thereby showing that the tissue scaffold of the present disclosure can effectively promote bone regeneration.

Figure 6:
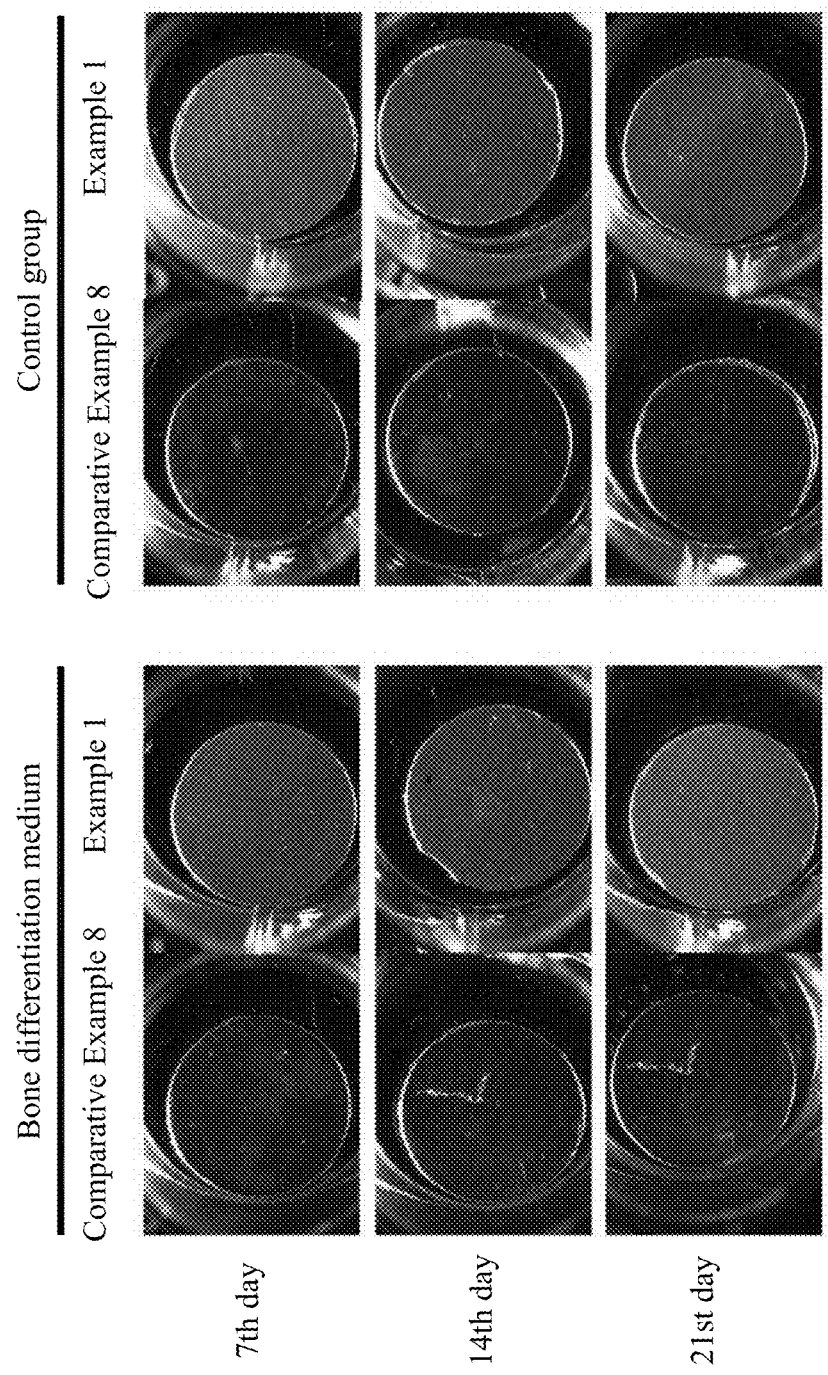
FIG. 6 is a comparison diagram of calcium deposition staining of the tissue scaffolds on the 7th, 14th and 21st day of cell culture of the embodiments and comparative examples according to the present disclosure.

(3) Determination of bone differentiation ability: mesenchymal stem cells (MSC) were used for a calcium deposition analysis. The cell seeding density was $5 \times 10^4/cm^2$, and the bone differentiation medium contained α-MEM containing 10% fetal bovine serum (FBS), ascorbic acid (50 µg/ml), dexamethasone (0.1 µM), and β-sugar phosphate (10 mM), while the control medium contained α-MEM containing 10% FBS. Samples were collected for analysis on the 7th, 14th and 21st days. After the cell samples were treated with the culture medium, they were stained with alizarin red to evaluate the calcium deposition on the 7th, 14th and 21st days, and recorded in FIG. 6. From the results in FIG. 6, it is shown that the calcium deposition is significantly increased due to the tissue scaffold comprising bioceramic materials of the present embodiment. It shows that the tissue scaffold of the present disclosure has the ability to promote bone differentiation of mesenchymal stem cells.

Next, the tissue scaffold prepared above was subjected to subsequent animal experiments.

Animal test of ligament reconstruction surgery: New Zealand white rabbits were used as the animal model of Medial Collateral Ligament (MCL) reconstruction surgery. Anesthetics (Zoleti150:Rompun20=1:1, 0.5 ml/kg) was used for anesthesia before surgery. The knee joint of the hind limb was opened with a scalpel, and drilled a bone tunnel in the femur and tibia, respectively. Then, the tissue scaffold was penetrated through the bone tunnel from the tibial end, and then penetrated into the femoral end of the bone tunnel. The tibial end was fixed with a metal button, and the femoral end was fixed with a metal bone nail. Finally, the separated layers of tissue and skin were sutured to complete the operation.

Figure 7A:
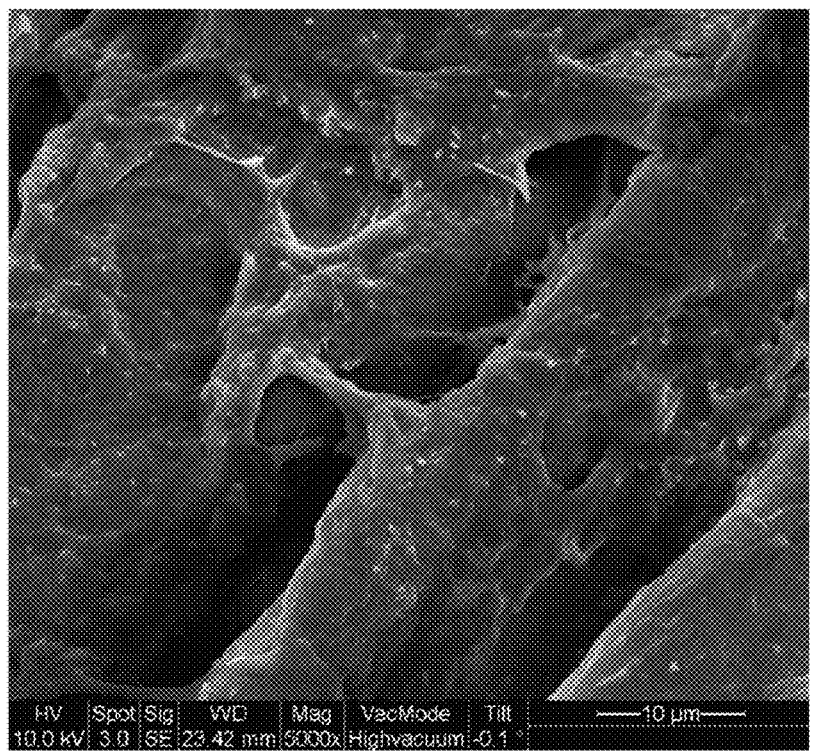
FIG. 7A to 7C are scanning electron microscope images of the regeneration of tendon and ligament tissue promoted by the tissue scaffold of the embodiments according to the present disclosure.
Figure 7B:
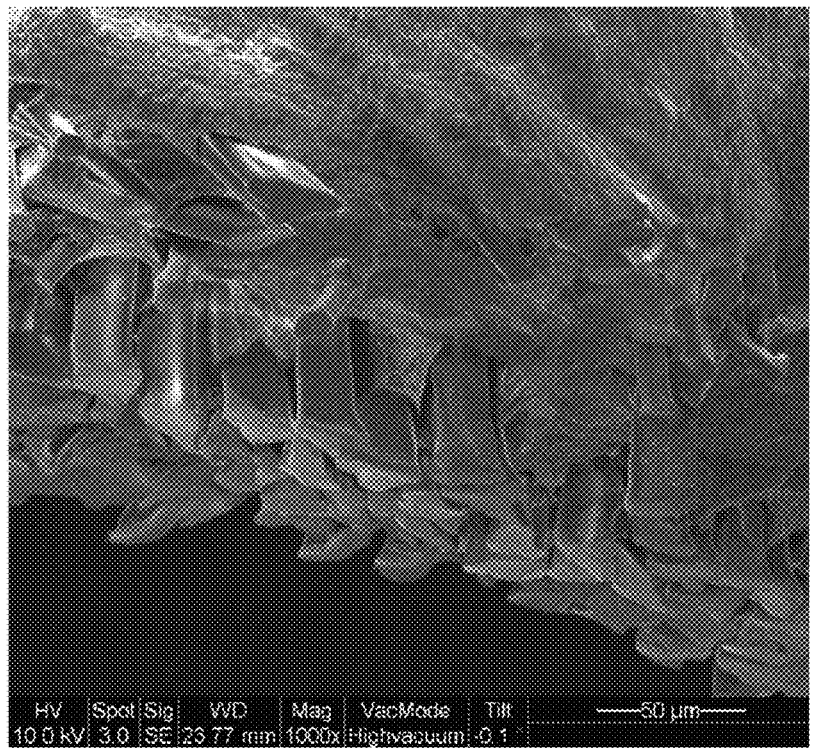
Figure 7C:
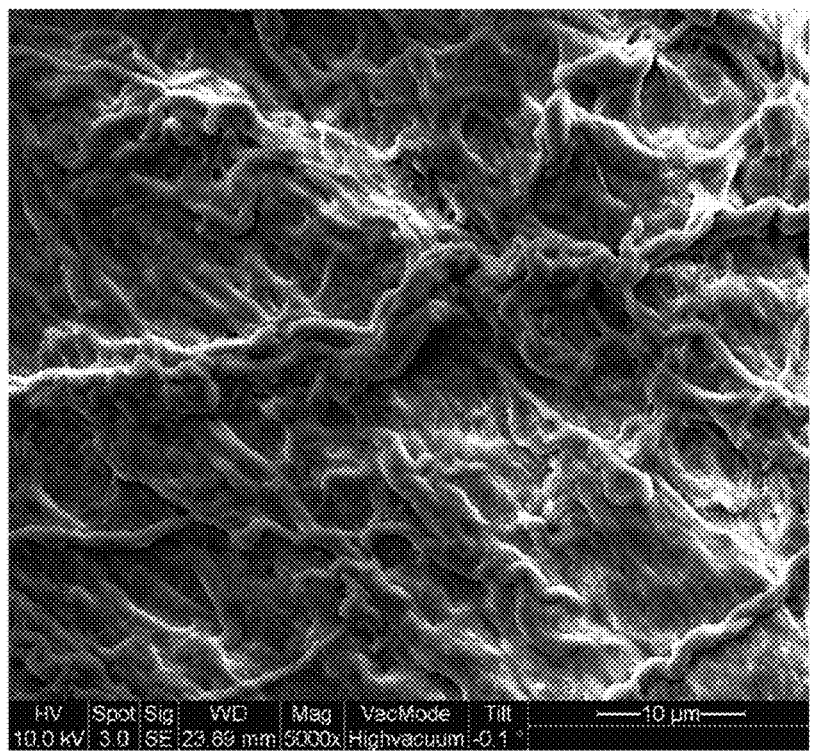
Figure 7D:
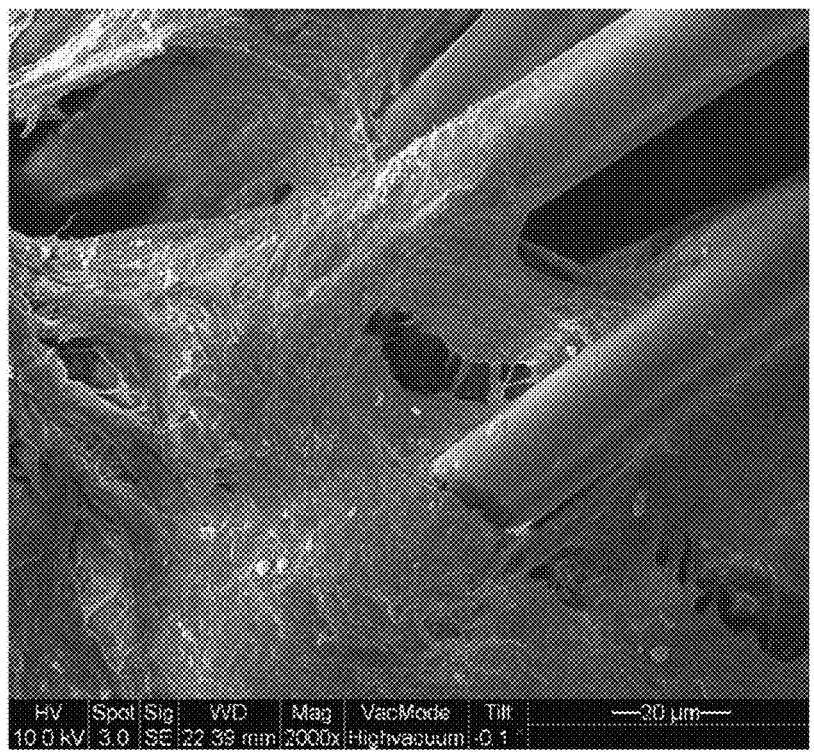
FIG. 7D to 7E are scanning electron microscope images of commercial tissue scaffolds.
Figure 7E:
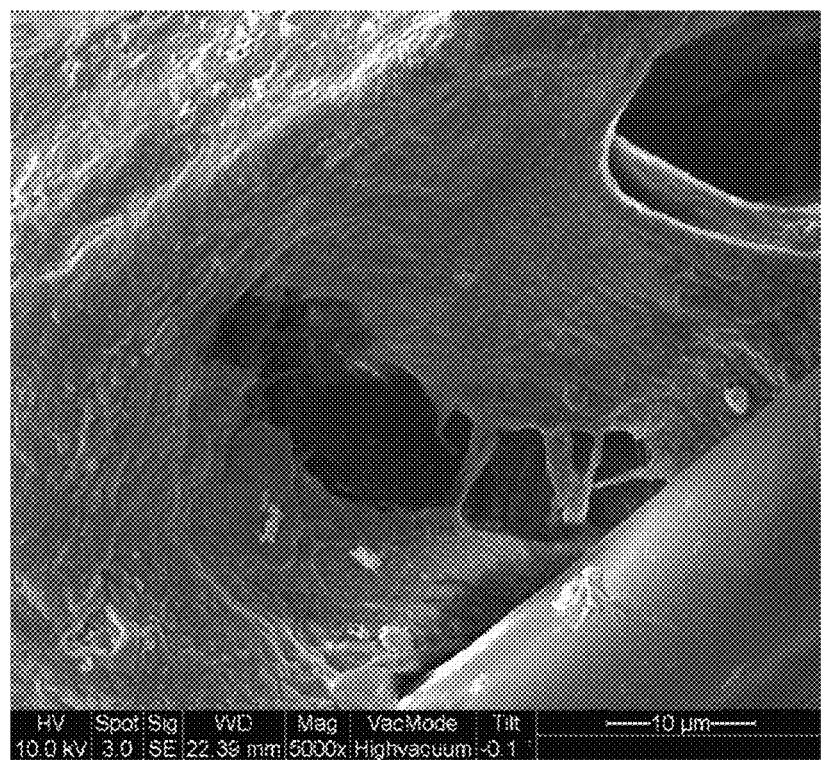

Finally, the following analysis on the implanted tissue scaffold of the above-mentioned animal experiment post 1 month or 3 months was performed:

(1) Scanning electron microscope: a scanning electron microscope (QUANTA 400F/Thermo Scientific™) was used to observe the tissue growth of the cross-section and surface of the implanted tissue scaffold in the animal experiment after 3 months. It is known from FIG. 7A that fibroblasts are observed on the fiber surface of the tissue scaffold of the present embodiment. In FIG. 7B and FIG. 7C, it is known that the collagen fiber soft tissue is distributed inside and on the surface of the tissue scaffold, forming a rope-like structure of tissue network and tightly covering the tissue scaffold of the present embodiment. It shows that the tissue scaffold of the present embodiment has excellent biocompatibility and biological activity, and can induce the regeneration of tendon and ligament tissue (fibroblasts and collagen fibers).

Figure 8B:
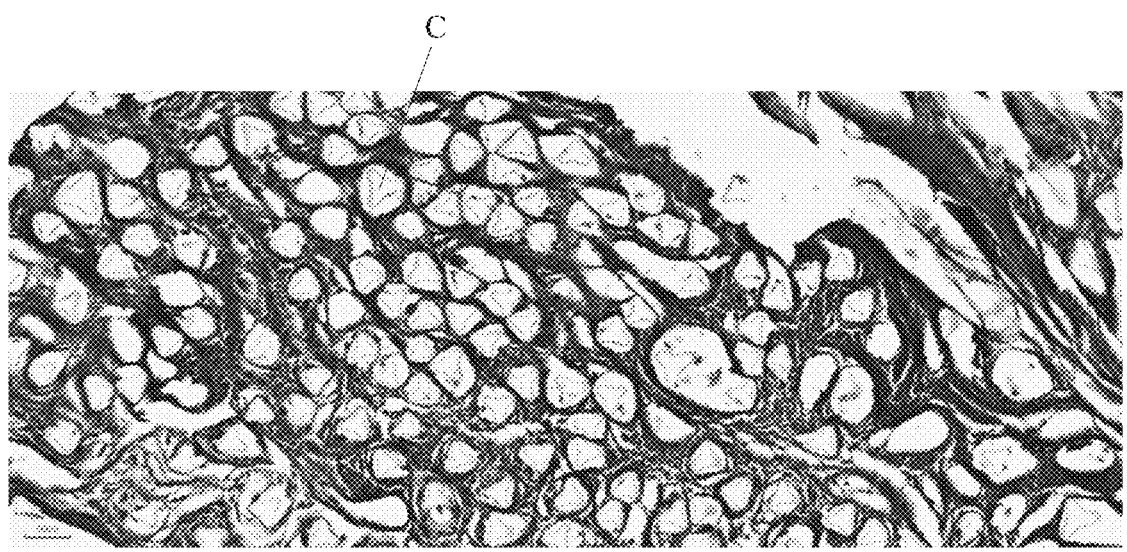
Figure 8C:
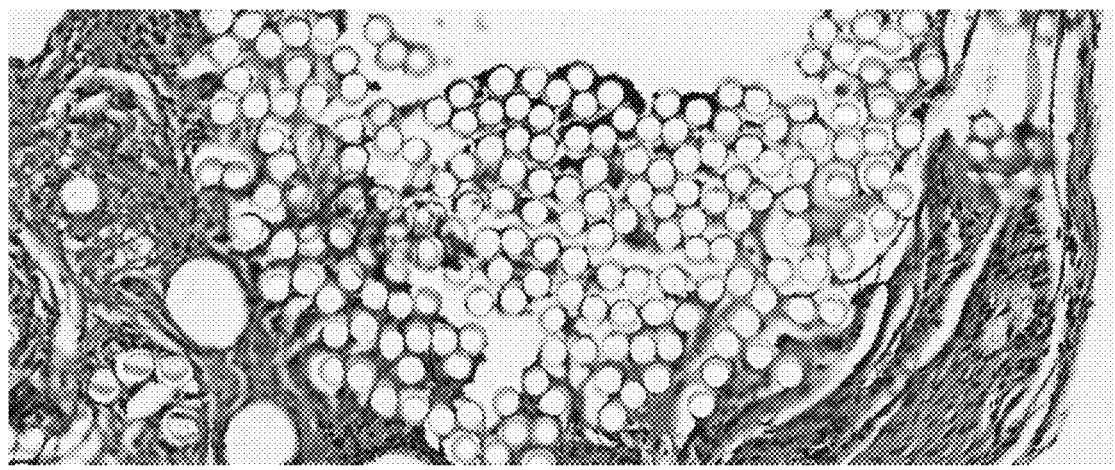
FIG. 8C to 8D are the tissue sections stained with hematoxylin-eosin and Masson's trichrome of the commercial scaffold, respectively.
Figure 8D:
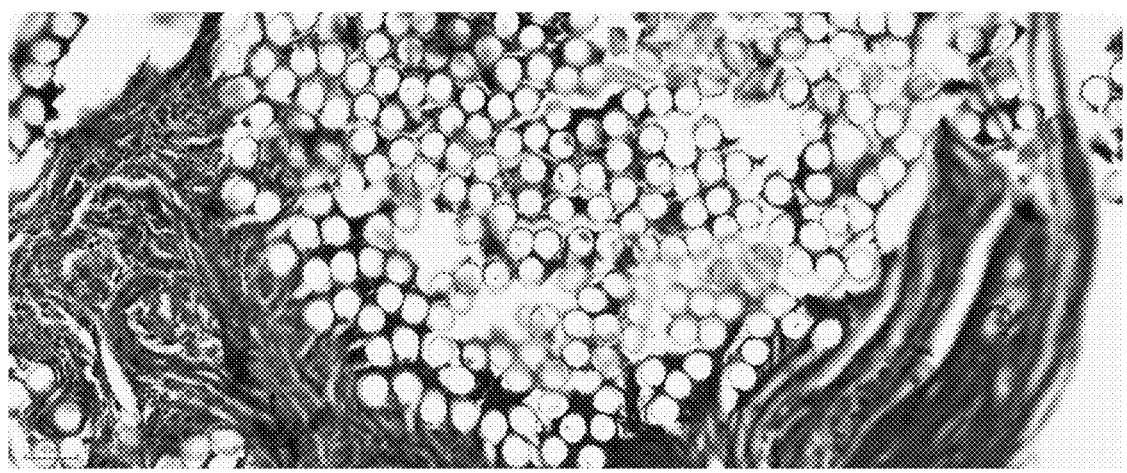

(2) Tissue section: The tissue including the implanted tissue scaffold was embedded in paraffin, sectioning along the radial direction of the warp yarns (for example, one of the tissue sections is as S in FIG. 1), then stained with hematoxylin-eosin and Masson's trichrome stain. Tissue growth of the implanted tissue scaffold in the animal experiment after 3 months. It is known that the peripheral and internal spaces of the tissue scaffold of the present embodiment are full of new cells and collagen fibrous tissue via both hematoxylin-eosin staining (FIG. 8A) and Mason's trichrome staining (FIG. 8B). It is obvious that the tissue scaffold of the present embodiment brings the effect of promoting the regeneration of tendon and ligament tissue (cells and collagen fibers), which means that the tissue scaffold is ligamented.

Figure 9A:
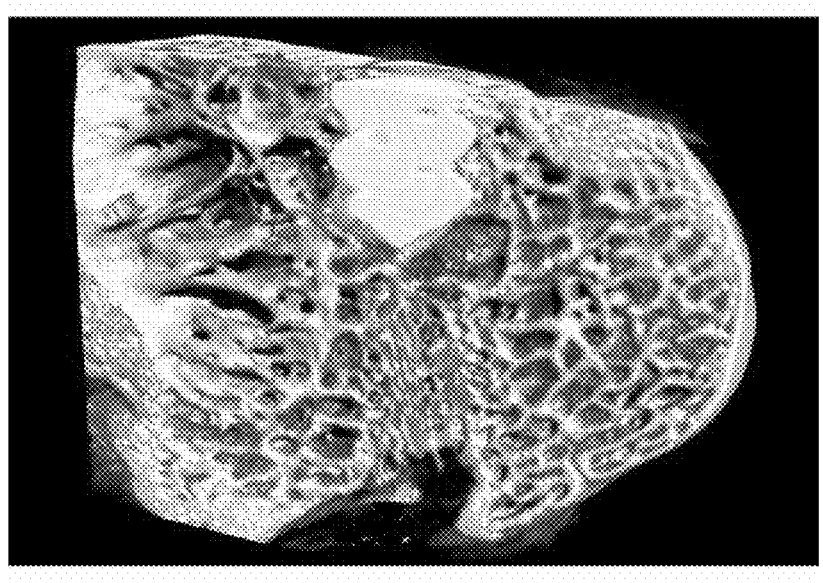
FIG. 9A to 9B are micro-computed tomography images of the osseointegration ability promoted by the tissue scaffold of the embodiments according to the present disclosure.
Figure 9B:
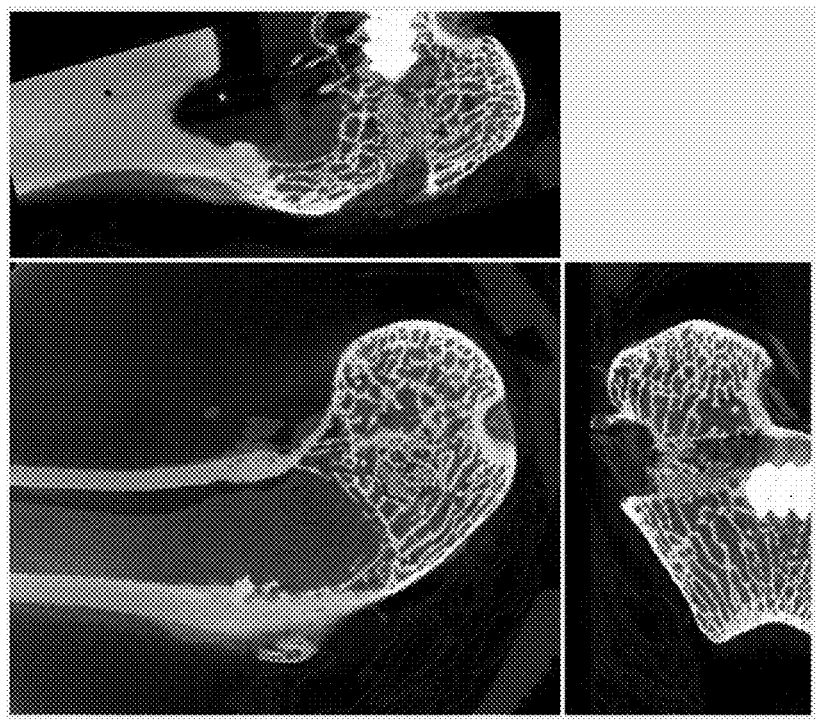
Figure 9C:
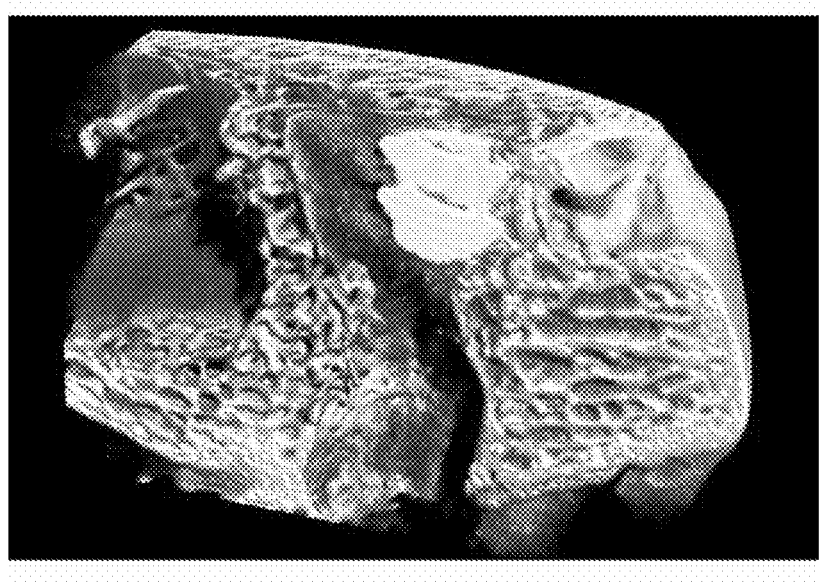
FIG. 9C to 9D are micro-computed tomography images of the commercial scaffold.
Figure 9D:
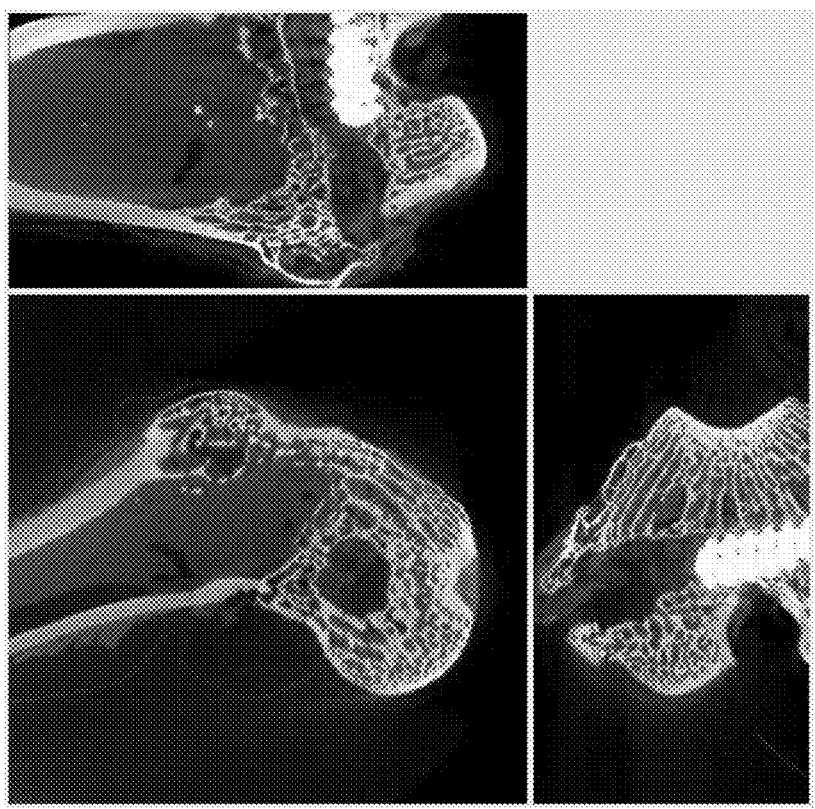

(3) Micro-computer tomography analysis (micro-CT): A micro-computer tomography (Bruker micro-CT, Kontich, Belgium) was used to analyze the tissue scaffold fixed in the bone tunnel of implantation in an animal experiment after 3 months. In FIGS. 9A and 9B, it is known that the tissue scaffold fixed in the bone tunnel of the present embodiment has formed a new bone. It is obvious that the tissue scaffold of the present embodiment has the ability to heal the interface between the implant and the bone (meaning it has the ability of osseointegration).

Figure 10:
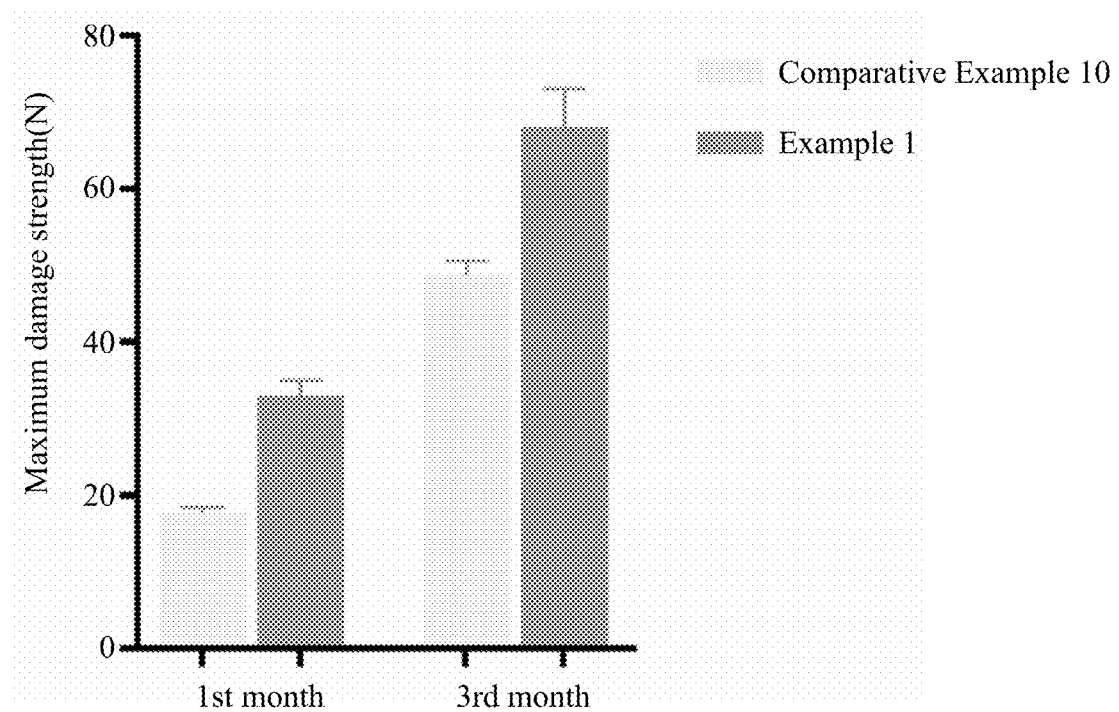
FIG. 10 is a comparison diagram of the mechanical strength of the tissue scaffolds in the bone tunnel in the first month and the third month of the embodiments and the comparative examples according to the present disclosure.

(4) Biomechanics test: a tensile testing machine (IN-STRON 3400) was used to measure the mechanical strength of the tissue scaffold fixed to the bone tunnel. First, the metal button that fixes the specimen to the tibia was cut off, and then the specimen was moved to the test stage and fixed. The tissue scaffold was tested for the force for pulling out from the tibia or finally rupturing it, when it is implanted in animal experiments after 1 month and 3 months. As that in FIG. 10, due to the unique weave structure design and excellent osseointegration ability of the tissue scaffold of the present embodiment, it can withstand greater tensile tension, thus improve the mechanical properties of the tissue scaffold.

Examples 2 to 5: Different Cross-Sectional Structures of the Warp Yarn Fiber

The preparation method of the tissue scaffold is the same as in example 1, except that the cross-sectional structure of the warp yarn fiber was changed to H-shaped, S-shaped, W-shaped and cross-shaped respectively. Then, the prepared tissue scaffolds were used to determine the number of cell proliferation and analyze the cell attachment ratio, and are recorded in FIG. 3 and FIG. 4.

Example 6: Different Concentrations of Bioceramic Materials

The preparation method of the tissue scaffold was the same as in example 1, except that the content of the bioceramic material was 4%. Then, the prepared tissue scaffold was analyzed for the activity of osteogenic enzymes, and recorded in FIG. 5.

Comparative Example 1

The preparation method of the tissue scaffold was the same as in example 1, except that the cross-sectional structure of the warp yarn fibers was a circular cross-section. Then, the prepared tissue scaffold was used to determine the number of cell proliferation and analyze the cell attachment ratio, and is recorded in FIG. 3 and FIG. 4.

Comparative Example 2

The preparation method of the tissue scaffold was the same as in example 1, except that the surface of the main body area of the weave was not modified. Then, the prepared tissue scaffold was used to determine the number of cell proliferation and analyze the cell attachment ratio, and are recorded in FIG. 3 and FIG. 4.

Comparative Examples 3 to 7

The preparation method of the tissue scaffold was the same as in Comparative Example 2, except that the cross-sectional structure of the warp yarn fiber was changed to a circular cross-section, a H-shaped cross-section, a S-shaped cross-section, a W-shaped cross-section, and a cross-shaped cross-section, respectively. Then, the prepared tissue scaffolds were used to determine the number of cell proliferation and analyze the cell attachment ratio, and are recorded in FIG. 3 and FIG. 4.

Comparative Example 8

The preparation method of the tissue scaffold was the same as in example 1, except that the bioceramic material was not added. Then, the prepared tissue scaffold was analyzed for the activity of osteogenic enzymes, which is recorded in FIG. 5.

Comparative Example 9

The preparation method of the tissue scaffold was the same as in example 1, except that the content of the bioceramic material was adjusted to 1%. Then, the prepared tissue scaffold was analyzed for the activity of osteogenic enzymes, which is recorded in FIG. 5.

Comparative Example 10

A commercial tissue scaffold (Orthomed, LCA60NEF) was used for the animal test of the ligament reconstruction surgery of example 1. Then, the tissue scaffold was analyzed by the surface observation, tissue section, micro-CT and biomechanical testing, etc. and the results are recorded in FIGS. 7D to 7E, 8C to 8D, 9C to 9D, and FIG. 10.

In summary, the present disclosure combines the corresponding bioactive materials according to different sections of the tissue scaffold to induce the regeneration of tendons or ligaments and at the same time improve the osseointegration ability. Accordingly, a tendon or a ligament tissue similar to autogenous ones is gradually formed, and the problems of fatigue, abrasion, rupture and poor stability of existing artificial grafts after long-term use are solved.

The foregoing embodiments are merely illustrative, and not used to limit the present disclosure. Anyone who is familiar with this technique can modify and change the above embodiments without departing from the spirit and scope of this disclosure. Therefore, the scope of protection of the claims of the present disclosure is defined by the scope of the appended claims attached to the present disclosure, and as long as it does not affect the effect and implementable purpose of the present disclosure, it should be included in the technical content of the present disclosure.

What is claimed is:

1. A tissue scaffold for use in a tendon and/or a ligament, comprising a weave formed by interlacing a warp yarn and a weft yarn, wherein the warp yarn comprises a plurality of fibers each with an alternative shaped cross section structure, wherein the alternative shaped cross section structure is a non-circular cross-section structure, and the weave comprises:

a main body area comprising a bioactive component on a fiber surface thereof; and a fixed area, wherein the fixed area is formed on both sides of the main body area, wherein the weft yarn of the fixed area comprises a bioceramic material accounting for 1 to 4% by weight of the total weight of the weft yarn of the fixed area, and the warp yarn of the fixed area is free from containing a bioceramic material.

2. The tissue scaffold for use in a tendon and/or a ligament as claimed in claim 1, wherein the warp yarn comprises a fiber with the alternative shaped cross section structure, and a diameter of a long axis of the fibers is 15 to 50 micrometers, and a diameter of each of the fibers of the weft yarn constituting the weave is 20 to 50 micrometers.

3. The tissue scaffold for use in a tendon and/or a ligament as claimed in claim 1, wherein the alternative shaped cross section structure comprises a H-shaped section, a S-shaped section, a W-shaped section, a Y-shaped section or a cross-shaped section.

4. The tissue scaffold for use in a tendon and/or a ligament as claimed in claim 1, wherein a fineness of the warp yarn comprising the fiber with the alternative shaped cross section structure is 1.5 to 50 denier, and a fineness of the fibers of the weft yarn constituting the weave is 40 to 100 denier.

5. The tissue scaffold for use in a tendon and/or a ligament as claimed in claim 1, wherein a pore size of the weave is 0.1 to 1 mm.

6. The tissue scaffold for use in a tendon and/or a ligament as claimed in claim 1, wherein the material of the weave comprises polyethylene terephthalate, polyethylene, polytetrafluoroethylene, polyurethane, or a combination thereof.

7. The tissue scaffold for use in a tendon and/or a ligament as claimed in claim 1, wherein the bioactive component comprises collagen, and collagen accounts for 0.5 to 5% by weight of the total weight of the main body area.

8. The tissue scaffold for use in a tendon and/or a ligament as claimed in of claim 1, wherein the bioceramic material comprises calcium phosphate, calcium sulfate, bioglass, or a combination thereof.

9. The tissue scaffold for use in a tendon and/or a ligament as claimed in claim 1, wherein the bioceramic material is hydroxyapatite, and an average particle size thereof is 10 to 200 nanometers.

* * * * *